United States Patent [19]
Gallant et al.

[11] 3,980,944
[45] Sept. 14, 1976

[54] PORTABLE CONDUCTIVITY METER FOR ARTIFICIAL KIDNEY MACHINES

[75] Inventors: Stuart L. Gallant, Minneapolis; Louis C. Cosentino, Wayzata, both of Minn.

[73] Assignee: Renal Systems, Inc., Minneapolis, Minn.

[22] Filed: Nov. 8, 1974

[21] Appl. No.: 522,102

[52] U.S. Cl. .............................. 324/30 R; 204/271; 324/30 B
[51] Int. Cl.² ......................................... G01N 27/30
[58] Field of Search ............. 324/30 R, 30 B, 65 R, 324/65 P, 72.5, 93; 204/271

[56] References Cited
UNITED STATES PATENTS

| | | | |
|---|---|---|---|
| 3,029,379 | 4/1962 | Ingram | 324/30 R |
| 3,412,325 | 11/1968 | Soderling | 324/65 P |
| 3,549,989 | 12/1970 | Brown | 324/30 B |
| 3,748,899 | 7/1973 | Gregg et al. | 324/30 B |
| 3,870,952 | 3/1975 | Sibley | 324/65 R |

Primary Examiner—Ronald J. Stern
Assistant Examiner—Wm. H. Punter
Attorney, Agent, or Firm—Merchant, Gould, Smith, Edell, Welter & Schmidt

[57] ABSTRACT

An improved portable conductivity meter for automatically and rapidly drawing an electrolyte sample and for measuring and providing an accurate output indication of its electrical conductivity, which is independent of temperature variations of the electrolyte. A pen-like dip probe, housing an electrode pair and a thermistor in unique configuration, is designed to rapidly draw an electrolytic dialysate sample whenever the probe is immersed within the electrolyte. A high frequency AC source drives a balanced active measurement circuit, having a reference leg and a measurement leg which contains the electrode pair and the temperature compensating thermistor. The balanced circuit provides measurement and reference output signals of opposite polarity to a summing amplifier which drives a visual conductivity indicator.

14 Claims, 7 Drawing Figures

FIG. 7

PORTABLE CONDUCTIVITY METER FOR ARTIFICIAL KIDNEY MACHINES

BACKGROUND OF THE INVENTION

1. Scope of the Invention

This invention relates generally to conductivity meters and more particularly to a portable conductivity meter for automatically accurately and repeatably measuring the conductivity of an electrolyte used in artificial kidney machines.

2. Description of the Prior Art

Conductivitity meters for measuring the electrical conductivity of electrolytic dialysate solutions for artificial kidney machines are known in the art. Most prior art conductivity meters are stationary apparatus having a conductivity cell or a pair of electrodes, permanently affixed to a housing submersed within an electrolyte, and electrically connected with a stationary control apparatus or other piece of peripheral equipment for providing an output control signal responsive to the conductivity cell or electrode measurement. The conductivity meters, while designed to adequately measure the electrolyte conductivity within that particular electrolyte container with which they are used, generally do not provide accurate and repeatable conductivity measurements without recalibration if used with electrolyte containers having configurations different from that for which the meter was previously calibrated. Similarly, recalibration of the meter will be required if the position of the electrodes relative the walls of the same electrolyte container is changed. These results are due to the fact that conductivity measurements made via electrode pairs are inherently sensitive to the size and shape of the electric field developed therebetween, (i.e. to the "effective volume" of electrolyte sample seen by the electrodes). The size and shape of the electric field developed between the electrodes necessarily varies as a function of the size and configuration of the electrolyte container and with the relative positioning of the electrodes therein.

A portable conductivity meter overcomes many of the disadvantages of the stationary single purpose conductivity meters and is intended to provide rapid mobile conductivity measurement of any portion of a larger electrolyte sample. Such portable conductivity meters are required in many applications wherein a stationary conductivity meter is not required, to check the accuracy of a stationary conductivity meter permanently implanted within the electrolyte, to provide a rapid accurate conductivity reading of the electrolyte for qualifications or test purposes, or the like. While providing increased flexibility of use advantages, prior art portable conductivity meters which have expanded scales required for accurately measuring conductivity over a narrow conductivity range, have generally been expensive and have not displayed the stability or repeatability required for such applications.

While accuracy and repeatability can oftentimes be sacrificed, there are certain applications wherein there is absolutely no room for error in either the accuracy or repeatability of a conductivity measurement. One such application is in the conductivity measurement of a dialysate electrolyte employed for use within an artificial kidney system. In such systems, the conductivity of the dialysate provides an accurate indication of the ionized salts (such as sodium chloride) present within that dialysate. Such salt concentrations must be accurately known within an artificial kidney system to provide proper operation of the artificial kidney machine in the hemodialysis process, on an individual patient requirement basis. Since the required dialysate conductivity for an artificial kidney system can differ from patient to patient, it becomes extremely important to have a portable conductivity meter available which can accurately and rapidly measure the dialysate conductivity, both in batch type and in proportioning type artificial kidney systems.

The primary disadvantages of prior art portable conductivity meters used for measuring the conductivity of dialysate electrolytes, have been their high cost inaccuracy, instability and nonrepeatability. One such prior art dialysate conductivity meter comprises a single hand-held chassis housing conductivity measurement circuits, having a conductivity indicator on an upper surface and a pair of electrodes projecting from its lower surface. This device only requires the operator to physically hold the chassis above the electrolyte sample such that the electrodes are immersed therein to effect a conductivity measurement, but suffers inaccuracies and nonrepeatability in measurement due to operator variances in positioning of the electrodes relative the walls of the electrolyte container, as above described with respect to the stationary conductivity meters.

Another prior art portable dialysate conductivity meter attempts to cure the inaccuracy and nonrepeatability problems of the above-described meter by defining a fixed measurement volume within the chassis of the meter, but requires a plurality of steps to be performed for making a measurement. This device employs a sample scoop member with which a sample of electrolyte is physically removed (scooped) from a larger batch thereof, and requires the operator to physically deposit the scooped electrolyte sampe into a chassis of the conductivity meter. The scoop member is designed such that its handle portion can be thereafter inserted within the conductivity meter chassis in such a manner so as to cause a thin volume of the scooped electrolyte sample to be formed between and to physically engage a pair of measurement electrodes, after which the actual conductivity measurement can be made. The conductivity measurement is made on the thus isolated electrolyte sample by passing a DC current between the electrodes and through the electrolyte sample. The DC current, however, electrolyzes the dialysate sufficiently so as to distort the conductivity reading. Therefore, besides requiring the operator to perform a plurality of measurement steps, this prior art device introduces inaccuracies into the measurement itself, casuing nonrepeatability in measurements.

The present invention overcomes the above disadvantages of both the stationary and the portable conductivity meters of the prior art, and offers a portable conductivity meter operable with rapid one-step operation to automatically provide an accurate dialysate conductivity measurement over a narrow conductivity range which is reliably repeatable over time.

SUMMARY OF THE INVENTION

A portable conductivity meter for making rapid and accurate dialysate conductivity measurements is provided, comprising a pen-like probe suitable for dipping within an electrolyte solution and operatively connected by means of a length of flexible cable to a chassis displaying a conductivity indicator. The pen-like probe contains an internal sample tube configured to automatically and raidly draw a sample of electrolyte solution therein whenever the probe is dipped within an electrolyte to be measured. A pair of electrodes and a thermistor project within the probe sample tube and are secured thereto in a unique manner so as to become completely immersed within the drawn electrolyte sample. A unique circuit pattern, bonded to the external surface of the sample tube is operatively connected to and, along with the flexible cable, provides electrical energization of the thermistor and electrode pair within the sample tube. Except for the internal chamber of the sample tube and for inlet and air release ports providing continuous ingress and outgress respectively thereto, the probe is completely sealed from exposure to external environments.

An electronic measurement circuit network is housed with the conductivity indicator, within the chassis for energizing the thermistor and probe electrodes and for providing an output indication of the conductivity of the electrolyte sample. An oscillator provides a high frequency AC signal output for driving an active balanced measurement circuit having a reference leg and a measurement leg. The reference leg produces a reference output signal to a summing junction output of the balanced circuit.

The probe electrodes are energized by the AC drive signal, forming an electrical conduction path through the drawn electrolyte sample therebetween. The impedance of the drawn electrolyte sample between the electrode pair is connected to provide the input impedance to a probe amplifier within the measurement leg of the balanced measurement circuit. The probe thermistor responds to temperature variations in the drawn electrolyte sample and is operatively connected within a feedback loop of the probe amplifier to exactly compensate for changes in the electrolyte impedance caused by temperature variations thereof. The measurement leg of the balanced circuit produces a measurement output signal to the summing junction, having opposite polarity of the reference output signal. Since the reference and measurement legs of the balanced measurement circuit are driven by a common AC source signal, and since the measurement and reference output signals are of opposite polarity, frequency and voltage variations in the source signal cancel at the summing junction. The summing junction is connected as the signal input terminal to a summing amplifier, connected to drive the output conductivity indicator to provide an accurate visual conductivity reading.

While a particular probe style and configuration for rapidly drawing an electrolyte sample will be disclosed, it will be understood that other probe configurations which provide like results could equally well be employed within the spirit and intent of this invention. Further, while particular electrical circuit configurations for generating an AC source drive signal and for providing amplification, filtering and detection within the preferred embodiment are disclosed, it will be understood that other comparable circuit configurations could equally well be employed.

BRIEF DESCRIPTION OF THE DRAWINGS

Referring to the Drawing, wherein like numerals represent like parts throughout the several views.

DESCRIPTION OF THE PREFERRED EMBODIMENT

Figure 1:
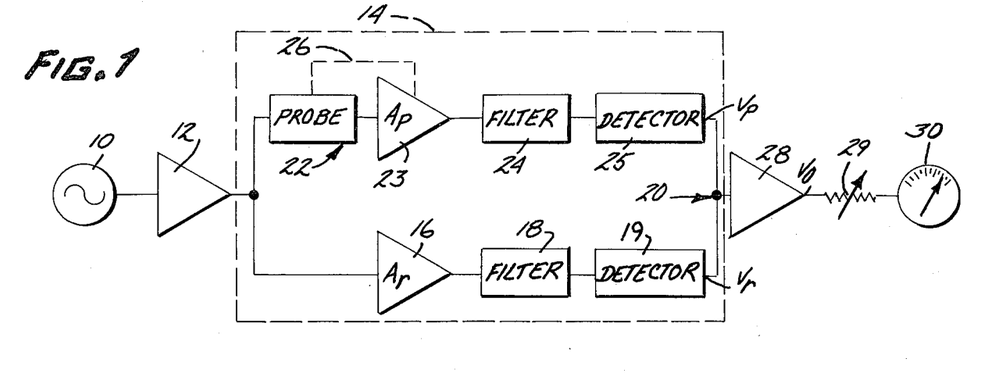
FIG. 1 is a diagrammatic representation of the functional blocks of the present invention.

Referring to the Drawing, there is generally illustrated in FIG. 1 a block diagram representation of the functional measurement analysis circuits of a preferred embodiment of the invention. An oscillator 10 supplies an AC drive signal by means of a buffer amplifier 12 to a balanced conductivity measurement circuit, generally designated at 14. The balanced conductivity measurement circuit 14 has a first ("reference") leg comprising a reference amplifier 16 serially connected with a reference filter 18 and a reference detector network 19, to provide a reference output signal ($V_r$) to a summing junction 20. The reference amplifier 16 has a gain $A_r$.

The oscillator 10 also energizes a second ("measurement") leg of the balanced conductivity measurement circuit 14 by means of a probe, generally designated at 22. Circuit elements within the probe 22, to be described hereinafter in detail, provide energization of a probe amplifier 23 serially connected with a probe filter 24 and a probe detector network 25 to provide a probe output signal ($V_p$) to the summing junction 20. For ease in distinguishing functional circuit elements within the reference leg verses those within the measurement leg of the balanced circuit 14, the amplifier, filter and detector networks 23, 24 and 25 respectively within the measurement leg have been preceded by the identifier "probe"; whereas the amplifier, the filter and the detector 16, 18 and 19 respectively within the reference leg of the balanced circuit 14 have been preceded by the identifier reference.

The probe amplifier 23 has a gain generally designated as $A_p$, which is determined in part by the electrical components within the probe 22, as illustrated by the dashed line 26 extending between the probe 22 and the probe amplifier 23.

The signals applied to the summing junction 20 from the probe and reference detector networks 25 and 19 respectively are amplified by means of a summing amplifier 28. The output signal $V_o$ from the summing amplifier 28 is applied by means of a potentiometer 29 to drive a conductivity measurement indicator, generally designated at 30.

Figure 2:
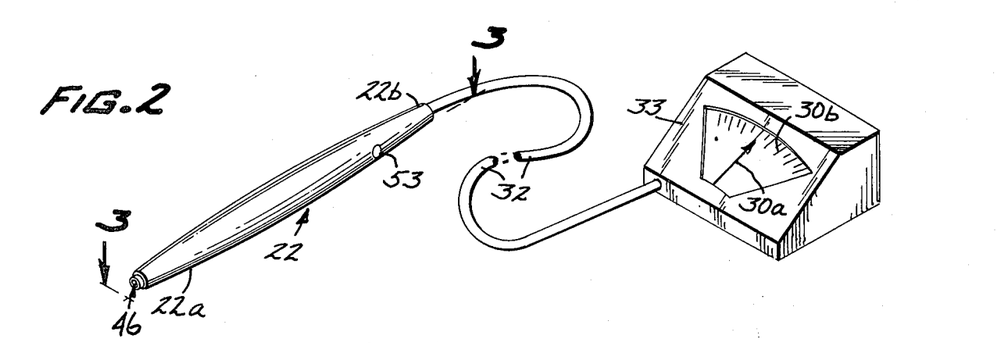
FIG. 2 is a perspective view of the dip probe and of the conductivity indicator portions of the present invention, disclosed in FIG. 1.

Referring to FIG. 2, the probe 22 is illlustrated in perspective view as it appears in the preferred embodiment. The probe 22 is an elongated pen-shaped hand-held member having a lower end 22a suitable for imersion into an electrolyte whose conductivity is to be measured, and an upper end 22b from which projects a flexible electrical cable 32. The cable 32 extends between the upper probe end 22b and a chassis 33, and provides electrical conduction therebetween, as described in more detail later herein. The chassis 33 contains all of those electrical networks disclosed in FIG. 1, with the exception of the electrical components located within the probe 22. The chassis 33 is sized for ease of carrying in one hand and houses its own portable battery power (not illustrated) for energizing the electrical circuits therein and the electrical components within the probe 22.

The conductivity measurement indicator 30 is housed within the chassis 33 so as to provide a readibly visible indication of the electrolyte conductivity for any measurement made. The conductivity measurement indicator 30 of the preferred embodiment is a standard meter type movement, having an indicator needle 30a traversing a conductivity scale 30b graduated in units of mhos per unit length over a conductivity range that will vary, depending upon the use to which the conductivity meter is to be applied. In the preferred embodiment, the conductivity meter is employed to accurately measure the conductivity of a dialysate solution which varies between 11 millimhos/cm to 15 millimhos/cm; accordingly, the conductivity scale 30b is graduated to indicate readings over a range of 11 to 15 millimhos/cm.

The elongated pen-shaped design of the probe 22 enables ease of grasp and manipulation by its user, and as designed, it can be completely immersed within an electrolyte without damage thereto or to any of its electrical measurement circuits. The cable 32 is of flexible material sufficient in length to allow electrolyte samples to be drawn by the probe 22 at distances well removed from the chassis 33.

Figure 3:
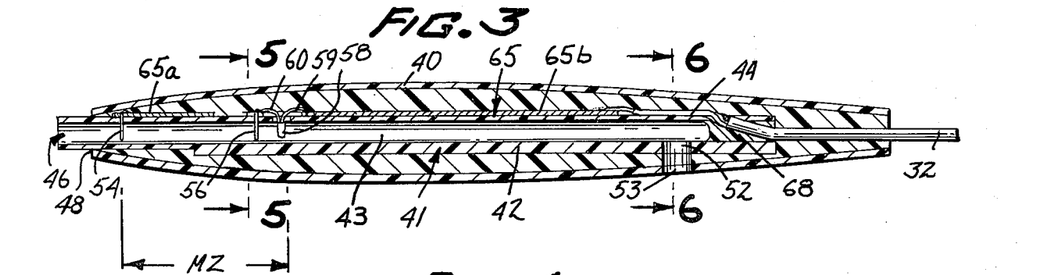
FIG. 3 is an enlarged sectional view, with portions thereof broken away, taken along line 3—3 of the hand-held probe illustrated in FIG. 2.
Figure 4:
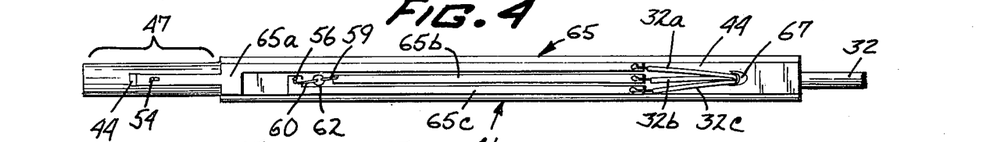
FIG. 4 is a plan view, of the sample tube and inlet nozzle portions of the dip probe illustrated in FIG. 3.
Figure 5:
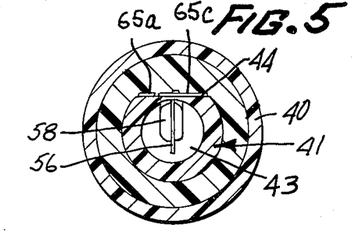
FIG. 5 is a vertical cross-sectional view generally taken along the line 5—5 of the dip probe illustrated in FIG. 3.
Figure 6:
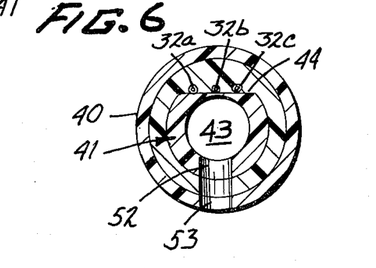
FIG. 6 is a vertical cross-sectional view, generally taken along the line 6—6 of the dip probe illustrated in FIG. 3.

The probe 22 is illustrated in more detail in FIGS. 3 through 6. Referring thereto, the probe 22 generally has an external pen-shaped casing 40 enclosing a sample tube 41, longitudinally extending within the casing 40. The external casing may be of any configuration and style suitable for protecting the more delicate enclosed sample tube 41. In the preferred embodiment, the sample tube 41 has a generally cylindricallly shaped external tube wall 42 having a flattened upper portion 44 and enclosing an internal chamber 43, as illustrated in FIGS. 5 and 6. While the sample tube 41 is formed of plexiglass in the preferred embodiment, it will be understood that other suitable materials could equally well be employed within the spirit and intent of this invention.

The external wall 42 of the sample tube 41 defines an inlet port 46 which extends through the external wall 42 and opens into the inner chamber 43. The foremost portion (47) of the sample tube adjacent the inlet port 46 thereof has a reduced outer diameter, and projects from the main body of the sample tube 41 through an opening 48 in the foremost portion 22a of the pin-like casing 40. The inside diameter of the foremost portion 47 is identical to that of the main body of the sample tube 41, forming a continuous surface of the internal chamber 43 therewith. The upper flattened portion 44 of the sample tube 41 also extends along most of the forward portion 47 of the tube 41, as illustrated in FIG. 4.

The external wall 42 of the sample tube 41 also defines an air release port 52 (see FIGS. 2 and 6) into the inner chamber 43 of the sample tube 41. The air release port 52 is aligned with an opening 53 in the external casing 40 (hereinafter described in more detail) to provide a second unobstructed passage from the external environment into the inner chamber 43.

First and second electrodes 54 and 56 (FIGS. 3 – 6) extend through the flattened upper portion 44 of the sample tube wall 42 and downwardly project within the inner chamber 43 of the sample tube 41. In the preferred embodiment, the first and second electrodes 54 and 56 are platinum alloy wire elements which are ideally suited for long-life and reliable operation when used with highly corrosive electrolytes, but could equally well be made of other conductive materials within the spirit and intent of this invention. The electrodes 54 and 56 are positioned within the inner chamber 43 of the sample tube 41 through pre-drilled holes (not illustrated) through the flattened upper portion 44 of the sample tube 41 and are fixedly secured therein via epoxy or the like to prevent leakage of electrolyte through the securing holes.

A thermistor 58 (diagrammatically illustrated in FIGS. 3 – 5) also extends within the inner chamber 43 of the sample tube 41 for complete immersion thereof within an electrolyte sample filling the inner chamber 43 during a conductivity measurement test. The thermistor 58 is inserted into its desired position within the inner chamber 43 through a hole 62 in the flattened upper portion 44 of the tube 41, which is thereafter sealed via epoxy or other suitable sealant, so as to suspend the thermistor 58 within the internal chamber 43 by a pair of first and second output terminals 59 and 60 respectively of the thermistor 58, as illustrated in FIGS. 3 and 5.

Referring to FIGS. 4 through 6, the flattened upper portion 44 of the sample tube 41 has a conductor pattern, generally designated at 65, secured thereto and providing electrical connections and energization paths for the first and second electrodes 54 and 56 respectively and for the thermistor 58 by means of its first and second output terminals 59 and 60 respectively. In the preferred embodiment, the conductor pattern 65 comprises three conductor paths 65a, 65b, and 65c secured to and longitudinally extend along the outer flattened portion 44 of the sample tube 41, as illustrated in FIG. 4. In the preferred embodiment, the conductor patterns 65 are physically glued to the sample tube 41; however, it will be understood that many other conductor pattern techniques, such as the use of conventional printed circuit technology, flexible conductor circuit techniques, thin and thick film techniques, and the like, could all be used in the spirit and intent of this invention to provide the sample tube 41 with a conductor pattern. Also, it should be noted that the conductor pattern could be directly screened, deposited, pringed, etc. directly upon the outer surface of the sample tube 41 without the need for any intermediary substrate. The first electrode 54 (FIG. 4) is electrically connected to the conductor 65a. The first output terminal 59 of the thermistor 58 is electrically connected to the conductor 65b. The second electrode 56 and the second output terminal 60 of the thermistor 58 are electrically connected to the third conductor 65c.

The conductors 65a, 65b and 65c longitudinally extend along the length of the upper flattened portion 44 of the sample tube 41 and terminate at a position near the upper end 22b of the probe 22. These terminated ends of the conductors 65a, 65b, and 65c are respectively soldered to conductors 32a, 32b, and 32c within the cable 32 and provide electrical conduction paths from the conductor pattern 65 to the electrical circuits with the chassis 33, as hereinafter described. For future ease in describing the electrical signal flow paths from the probe 22 to the circuits within the chassis 33, only the cable conductors 32a – c will be called out, it being understood that the conductor pattern 65 is present for providing continuous electrical conduction from the cable 32 to the pair of electrodes 54 and 56 and to the thermistor 58.

In the preferred embodiment, the cable 32 projects through a hole 67 in the outer wall 42 near the upper end 22b of the sample tube 44, and passes through the upper end of the sample tube 41 as illustrated in FIGS. 3 and 4. An epoxy seal 68 (FIG. 3) secures the cable 32 to the sample tube 41 and simultaneously seals the upper end of the inner chamber 43 at a point above the air release hole 52. This configuration, of passing the cable 32 through the sample tube wall and of securing it thereto provides mechanical protection to electrical solder connections of the wires 32a, 32b, and 32c respectively to the conductors 65a, 65b, and 65c respectively of the conductor pattern 65.

In the preferred embodiment, the probe assembly 22 is constructed as follows. The foremost end of the sample tube 41 is thinned down and drawn out to form the portion of reduced outer diameter (47). The plexiglass sample tube 41 is milled on one side to form the upper flattened portion 44. The insertion holes for the electrodes 54 and 56, the hole 62 for the thermistor 58 and the hole 67 for the cable 32 are drilled in the upper flattened portion 44 of the tube 41. The air outlet port 52, is drilled in the bottom of the tube 41. The electrodes 54 and 56 and the thermistor 58 are inserted into the sample tube 41 through their respective holes and are suspendedly secured therein by an epoxy sealant. The conductor pattern 65 is secured to the upper flattened portion 44 of the tube 41 and the electrodes 54 and 56 and the terminals 59 and 60 of the thermistor 58 are appropriately soldered thereto. The cable 32 is inserted through its hole 67 and is electrically and mechanically connected in place. Following the above assembly steps, the entire sample tube 41 and assembly is inserted within the casing 40 of the probe 22 such that the reduced diameter inlet portion 47 of the tube 41 protrudes through the opening 48 in the casing 40 at the lower end 22a of the probe 22, and such that the cable 32 extends from the upper portion 22b of the probe 22. The air release port 52 of the sample tube 41 is then aligned with the opening 53 in the casing 40 and an alignment plug (not illustrated) is inserted through the port 52 and the hole 53 to maintain alignment thereof. The entire inner portion of the casing 40 is then backfilled with epoxy to secure the sample tube 41 within the casing 40 while electrically insulating the conductor pattern 65 and its associated connections from the external environment. After the epoxy has cured the alignment plug which was inserted within the air outlet port 52 and the casing hole 53 is removed, establishing a continuous channel from the inner chamber 43 of the sample tube 41, through the air outlet port 52 and the opening 53 in the casing 40 to the external environment. It will be understood that while a specific assembly sequence has been disclosed, other assembly processes could equally well be employed within the spirit and intent of this invention. Further, while the entire inner portion of the casing 40 is backfilled with epoxy to effect a seal and electrical isolation of the sample tube 41 assembly, other techniques such as conformal circuit coating and "O" ring sealing assemblies or the like could equally well be employed within the spirit and intent of this invention.

In the preferred embodiment, the inner chamber 43 of the sample tube 41 is cylindrically shaped and has an inside diameter of 0.125 inch. The length of the electrodes 54 and 56 is also approximately 0.125 inch with a separation spacing of approximately 0.75 inch. The electrodes 54 and 56 and the thermistor 58 are secured near the lower portion 22a of the probe 22 to enable an accurate electrolyte conductivity reading to be made by merely dipping the probe 22 a distance of one inch into the electrolyte.

The spacing required between the electrodes is determined in part by the inside diameter of the inner chamber 43 of the sample tube. By providing a fixed volume sample tube having a small diameter, as in the preferred embodiment, the effective electrolyte impedance seen by the measurement circuits, as hereinafter described, is proportionately higher, thus minimizing the impedance effects of the electrodes themselves in the measurement.

Figure 7:
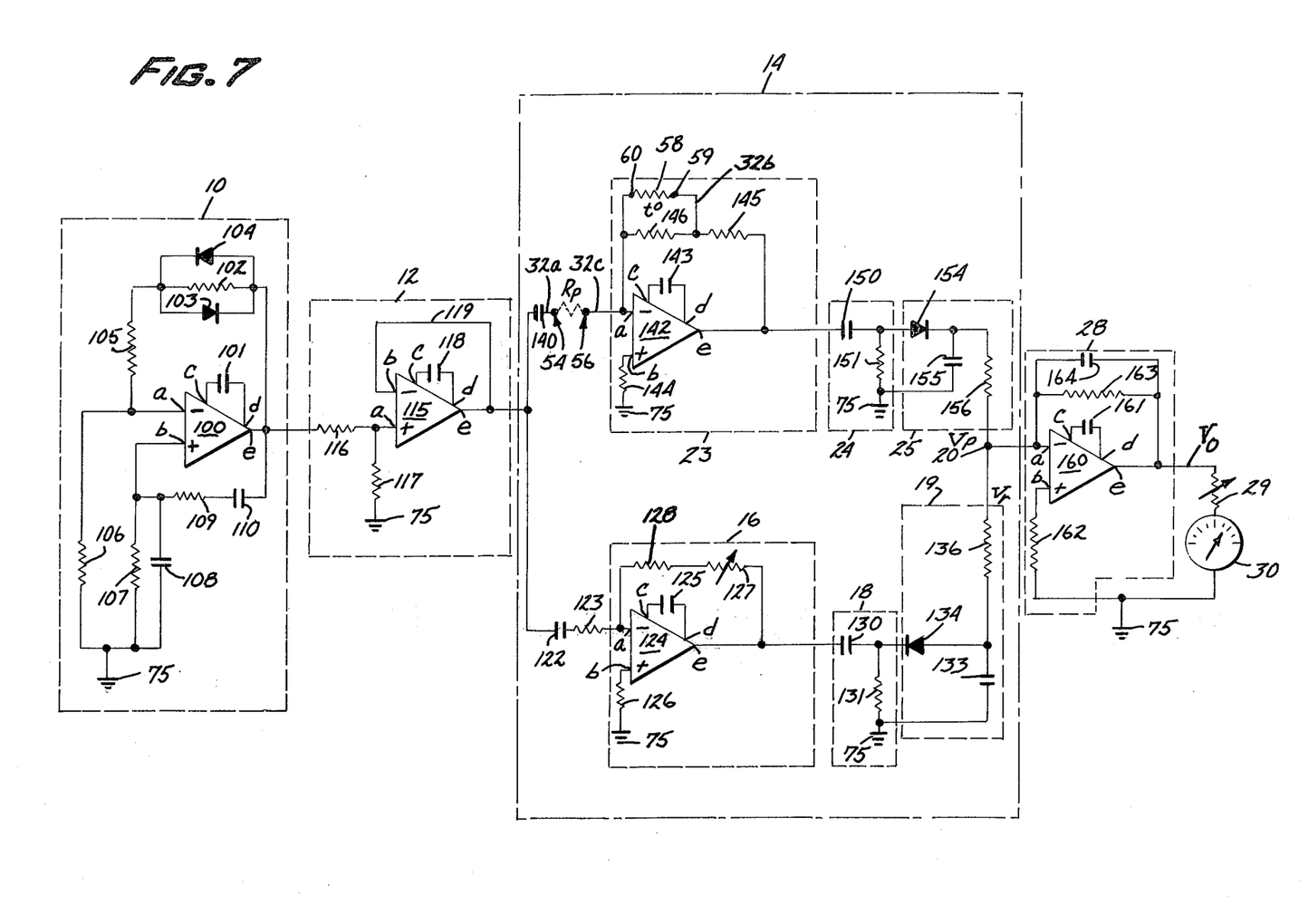
FIG. 7 is a schematic representation of the measurement analysis circuits of the preferred embodiment of the invention, disclosed in FIG. 1.

The conductivity measurement circuits of the preferred embodiment disclosed in FIG. 1 are illustrated in more detail in FIG. 7. Referring to FIGS. 1 and 7, the oscillator 10 is, in the preferred embodiment, a Wien bridge oscillator, which develops a fixed frequency by means of an operational amplifier 100. The amplifier 100 has an inverting (−) input 100a, a non-inverting (+) input 100b a pair of stabilizing inputs 100c and 100d and a signal output 100e. Unless otherwise specified, all operational amplifiers employed in the preferred embodiment are of the type LM301; however, it will be understood that other amplifiers could equally well be employed. Further, while power supply and ground connections are not illustrated in the Drawing, it will be understood that appropriate power supplies are present for energizing the electrical components and that the electrical components hereinafter described are appropriately connected for energization therefrom.

A stabilizing capacitor 101 is connected between the stabilization inputs 101c and 101d of the amplifier 100. The signal output 101e of the amplifier 100 is connected by means of a resistor 102 in parallel with a pair of oppositely directed diodes 103 and 104, all in series with a resistor 105 to the inverting (−) input 100a of the amplifier 100. The inverting (−) input 100a of the amplifier 100 is also connected by means of a resistor 106 to a common 75. The non-inverting (+) input 100b of the amplifier 110 is connected by means of a resistor 107 in parallel with a capacitor 108 to the common 75, and is also connected by means of a resistor 109 in series with a capacitor 110 to the signal output 100e of the amplifier 100. The resistors 107 and 109 and the capacitors 108 and 110 determine the frequency of oscillation of the oscillator 10, and can be selected to provide the desired oscillation frequency of the oscillator 10 as hereinafter described.

The signal output 100e of the amplifier 100 is connected by means of a resistor 116 to energize the non-inverting (+) input 115a of an operational amplifier 115 of the buffer amplifier 12. The non-inverting (+) input terminal 115a of the amplifier 115 is also connected by means of a resistor 117 to the reference 75. The amplifier 115 further has an inverting (−) input 115b, a pair of stabilization input terminals 115c and 115d and a signal output terminal 115e. A stabilizing capacitor 118 is connected between the stabilization input terminals 115c and 115d of the amplifier 115, and the amplifier 115 is connected as a unity gain amplifier by means of a feedback loop 119 connecting its output terminal 115e to its inverting (−) input 115b.

The signal output 115e of the amplifier 115 of the buffer amplifier 12 energizes the reference amplifier 16 within the leg of the balanced measurement circuit 14 by means of a coupling capacitor 122 in series with a resistor 123, connected to energize an inverting (−) input 124a of an operational amplifier 124. The amplifier 124 further has a non-inverting (+) input 124b, a pair of stabilization input terminals 124c and 124d and a signal output 124e. A stabilizing capacitor 125 is connected between stabilization input terminals 124c and 124d, and a resistor 126 connects the non-inverting (+) input terminal 124b of the amplifier 124 to the common 75. A variable resistor 127 and fixed resistor 128 are connected in series between the signal output 124e and the inverting (−) input 124a of the amplifier 124 to provide a feedback gain path.

The signal output 124e of the amplifier 124 is connected by means of a capacitor 130 in series with a resistor 131 to the common 75. The capacitor 130 and the resistor 131 form the filter 18 for providing high pass filtering of the signal output of the reference amplifier 16.

The signal output from the high-pass filter 18 is applied to the cathode of a diode 134 within the reference detector network 19. The anode of the diode 134 is connected by means of a capacitor 133 to the common 75 and is also connected by means of a resistor 136 to the summing function 20. The diode 134, the capacitor 133 and resistor 136, in combination, form a negative detection circuit for providing a reference output signal (Vr) to the summing junction 20.

The signal output from the output terminal 115e of the amplifier 115 of the buffer amplifier 12 energizes the circuits within the measurement leg of the balanced measurement circuit 14 by means of the first and second electrodes 54 and 56 respectively. The signal output 115e of the amplifier 115 is connected by means of a capacitor 140, the conductor 32a and the conductor pattern 65a (not illustrated) to energize the first electrode 54. The second electrode 56 is connected by means of the conductor pattern 65c (not illustrated) and the conductor 32c to an inverting (−) input 142a of an operational amplifier 142. The amplifier 142 further has a non-inverting (+) input 142b, a pair of stabilization input terminals 142c and 142d and a signal output terminal 142e. A stabilizing capacitor 143 is connected between the stabilization inputs 142c and 142d of the amplifier 142, and the non-inverting (+) input terminal 142b of the amplifier 142 is connected by means of a resistor 144 to the common 75.

A pair of serially connected resistors 145 and 146 provide a feedback amplification path from the signal output 142e of the amplifier 142 to its inverting (−) input terminal 142a. The thermistor 58 is also connected within the resistive feedback loop of the amplifier 142. The first output terminal 59 of the thermistor 58 is connected by means of the conductor pattern 65b (not illustrated in FIG. 7) and the conductor 32b to the junction of the resistors 145 and 146, and the second output terminal 60 of the thermistor 58 is connected by means of the conductor pattern 65c (not illustrated in FIG. 7) and the conductor 32c to the inverting (−) input terminal 142a of the amplifier 142. The gain determination for the probe amplifier 23 will be discussed in more detail hereinafter.

The output terminal 142e of the amplifier 142 is connected by means of a capacitor 150 in series with a resistor 151 to the common 75. The capacitor 150 and the resistor 151 or the filter 24 and provide high-pass filtering of the output signal of the probe amplifier 23.

The signal output of the probe amplifier 23, as filtered by the high-pass filter 24 is applied to the anode of a diode 154. The cathode of the diode 154 is connected by means of a capacitor 155 to the common 75 and is also connected by means of a resistor 156 to the summing junction 20. The diode 154, the capacitor 155 and resistor 156 in combination form a positive detection circuit 25 for providing a positive polarity probe voltage signal $V_p$ to the summing junction 20.

The output signals $V_r$ and $V_p$ from the reference and measurement legs respectively of the balanced circuit 14, are directly applied by means of the summing junction 20 to an inverting (−) input 160a of an operational amplifier 160 within the summing amplifier 28. Unlike the other amplifiers used in the preferred embodiment, amplifier 160 is a type LM308 The amplifier 160 further has a non-inverting (+) input terminal 160b, a pair of stabilization input terminals 160c and 160d and a signal outut terminal 160e. A stabilizing capacitor 161 is connected between the stabilization input terminals 160c and 160d, and the non-inverting (+) input terminal 160b of the amplifier 160 is connected to the common 75 by means of a resistor 162 in parallel with a damping capacitor 164. A feedback resistor 163 connects the signal output terminal 160e to the inverting (−) input terminal 160a of the amplifier 160.

The signal output 160e of the amplifier 160 and thus also of the summing amplifier 28 is directly connected by means of the potentiometer 29 to energize the meter movement of the conductivity measurement indicator 30. The movement of the indicator 30 connected for electrical reference to the common 75.

In the preferred embodiment, all of those circuits illustrated in FIG. 7 which are enclosed within the chassis 33 are conformally coated for protection against humidity and corrosion damage from exposure to salt containing environments.

In general, the portable conductivity measurement apparatus of the preferred embodiment provides an easy to use, highly accurate and stable means for measuring and providing an output indication of the electrical conductivity of a fixed volume of dialysate. The portable conductivity meter greatly facilitates the conductivity measurement process by enabling the operator to make his conductivity measurement in a simple one-step operation; he need only dip the measurement probe 22 into the electrolyte and the measurement circuits rapidly automatically provide an accurate output indication of the electrolyte conductivity by means of the indicator 30, as below described. Alternatively, should the operator desire to physically remove the sample of electrolyte to be measured from the larger volume or batch of electrolyte, he can so do by dipping the probe 22 into the electrolyte to a depth sufficient to enable the inner chamber 43 of the sample tube 41 to be filled with the electrolyte and by thereafter sealing the air outlet opening 53 of the probe casing 40 with his thumb or finger to create a partial vacuum within the inner chamber 43 as the probe 22 is raised from the electrolyte batch, to prevent the enclosed electrolyte from flowing out of the sample tube 41.

The probe 22 is uniquely designed to enable an electrolyte sample to be automatically drawn thereby, merely by dipping the probe 22 into a larger volume or batch of electrolyte. The operator can perform this operation by suspending the probe by the attached cable 32 from a point above the electrolyte batch and by simply lowering the probe 22 into the electrolyte batch. Due to the air release hole 52, in combination with the channel formed through the potting epoxy which cooperates with the hole 53 formed in the outer probe casing 40 a sample of electrolyte whose conductivity is to be measured automatically rapidly enters the inner chamber 43 of the sample tube 41 by means of the channel 50 in the inlet nozzle 47, whenever the probe 22 is dipped into the electrolyte. The electrolyte will fill the inner chamber 43 of the sample tube 41 to that same depth (measured from the lower end 22a of the probe 22) to which the probe 22 is immersed within the electrolyte. The air normally filling the inner chamber 43 is allowed to escape under pressure of the electrolyte entering the inner chamber 43, by means of the air release port 52. To enable a proper conductivity measurement of an electrolyte to be made, a sufficient sample of electrolyte must be drawn into the inner chamber 43 of the sample tube 41 so as to completely immerse the first and second electrodes 54 and 56 respectively and the thermistor proper 58 therein. For convenient referral thereto, this region within the inner chamber 43 of the sample tube 41 will hereinafter be referred to as the measurement zone, designated as MZ in FIG. 3; in the preferred embodiment, the dimensions used enable a complete conductivity measurement to be made by merely immersing the lower end 22a of the probe 22 approximately one inch into the electrolyte.

The probe 22, therefore, enables accurate, repeatable conductivity measurements to be made upon a fixed electrolyte volume which is physically isolated from the larger electrolyte volume or batch and is therefore insensitive to electrolyte movement or currents and other environmental effects of the batch which could adversely effect the conductivity measurement. Use of the probe 22 eliminates the problems of proper positioning of the conductivity cell or measurement electrodes, within the larger volume (batch) of electrolyte with respect to the particular configuration, size or material of the larger electrolyte holding container, which is a prime concern of prior art conductivity meters. While the probe configuration 22 provides a protective environment for the drawn electrolyte sample, in which a conductivity measurement can be made, accuracy of that measurement is not sacrificed due to any altering of the drawn electrolyte sample by the probe itself. For example, as will be described later herein, the conductivity measurement process compensates for changes in temperature of the electrolyte by means of the thermistor 58. While the temperature of the acutually drawn electrolyte sample may be altered slightly by its exposure to the inside walls of the sample tube 41, this alteration does not affect the accuracy of the conductivity measurement as long as the actual temperature of the drawn sample, whatever it may be, is accurately known. The thermistor 58 provides that function. The thermistor 58 is suspended within the inner chamber 43 of the sample tube 41 through the hole 62 in the upper flattened portion 44 of the sample tube 41 so as to be effected only by the temperature of the drawn electrolyte sample within the inner chamber 43 itself, as opposed to being effected by the temperature of the sample tube 41 or any by any of the related external assembly of the probe 22. Therefore, the temperature measured by the thermistor 58 truely indicates the temperature of the drawn electrolyte sample within the measurement zone MZ of the sample tube 41.

The probe 22 is further designed such that the entire portion of the probe 22 located between the external surface of the sample tube 41 and the internal surface of the probe casing 40 is sealed such that immersion of the entire probe 22 within the electrolyte batch cannot result in any damage to the probe 22 or its associated electrical components. These features, combined with the small size and ease of protability of the chassis 33 provide an extremely versatile measurement system, suitable for making rapid and accurate conductivity measurements in all types of environments wherein the electrolyte whose conductivity is to be measured, is physically accessible by the probe 22. In particular, the conductivity meter of this invention is particularly suitable for measuring the conductivity of the electrolytic dialysate of artificial kidney systems where the conductivity of the dialysate, indicating the percentages of ionized salts such as sodium chloride therein, must be very accurately known and controlled.

The electronic operation of the conductivity meter can be described with reference to FIGS. 1, 3, and 7. The conductivity meter is generally operable to measure the electrical conductivity of that fixed volume of drawn electrolyte sample present within the measurement zone MZ, and in particular, of that fixed volume of electrolyte within the measurement zone MZ located between the first and second electrodes 54 and 56 respectively. The effective volume of electrolyte within the measurement zone MZ and between the first and second electrodes 54 and 56 respectively, approximates a cylindrical volume as seen by the electrical meeasurement circuits (hereinafter described). The effective cylindrical volume is not perfect due to the shape of the actual electrical field lines which are developed within the sample of electrolyte between the first and second electrodes 54 and 56 respectively, as will become apparent hereinafter. However, as long as the volume, as defined by the sample tube 41 within the measurement zone MZ and between the electrodes 54 and 56 remains constant, once the electrical measurement circuits are calibrated with respect to that fixed volume for an electrolyte of known conductivity, the volume considerations thereafter are irrelevant, since that volume always remains constant.

The oscillator 10 provides a fixed frequency signal output, which is applied through the buffer amplifier 12 to simultaneously energize the circuits within the reference and measurement legs of the balanced conductivity measurement circuit 14. In the preferred embodiment, the frequency of oscillation of the oscillator is determined by the values of the resistors 107 and 109 in combination with the capacitors 108 and 110. The frequency range in the preferred embodiment varies from 10 to 15 khz; however, the particular frequency used will depend upon the application to which the conductivity meter is put. In practice, the upper frequency range available will be limited due to frequency degradation effects of the operational amplifiers within the measurement circuits at extremely high frequencies. However, higher frequency operation provides significant advantages in reducing the effects of harmful capacitances in the measurement process, and the use of an AC signal for driving the measurement electrodes (hereinafter described) minimizes polarization effects relative thereto.

The AC output signal from the oscillator 10, as buffered by the amplifier 12, drives the reference amplifier 16, by means of the coupling capacitor 122 in series with the input resistor 123. At the frequencies used, the impedance of the capacitor 122 is negligible with respect to the resistance of the input resistor 123. The AC signal output of the oscillator 10 also drives the probe amplifier 23 by means of the coupling capacitor 140 electrically in series with the first and second electrodes 54 and 56 respectively.

When an electrolyte sample whose conductivity is to be measured has been drawn into the inner chamber 43 of the probe sample tube 41 so as to fill the measurement zone MZ, an electrical conductivity path will be provided for the AC drive signal through the cylindrical volume of electrolyte sample between the first and second electrodes 54 and 56 respectively (see FIG. 3). When energized by the AC signal from the oscillator 10, the first electrode 54 will cause electric field lines to be established therefrom and extending to the second electrode 56 through the conductive electrolyte, establishing a conductive path therebetween. The electrical resistance of that conductive path through the electrolyte sample between the first and second electrodes 54 and 56 respectively is inversely proportional to the conductivity of the electrolyte sample and is directly measurable as hereinafter described. The electrolyte resistance between the first and second electrodes 54 and 56 respectively is designated in FIG. 7 and $R_p$. Therefore, the AC drive signal for the probe amplifier 23 will see an input equivalent circuit comprising the coupling capacitor 140 in series with the probe resistance $R_p$. At the frequency of the oscillator drive signal, the impedance of the coupling capacitor 140 is much less than that of the probe resistance $R_p$, and is negligible with respect thereto.

The length of the electrodes 54 and 56 relative the inside diameter of the inner chamber 43 of the sample tube 41 is selected such that the actual impedance of the platinum alloy electrodes is very small compared with the resistance of the electrolyte sample being measured ($R_p$). The physical lengths of the electrodes 54 and 56 relative the inside diameter of the inner chamber 43 are made as long as possible to minimize their impedance at the measurement frequency. Further, at the frequency of the drive signal from the oscillator 10, the electrode impedance becomes negligible with respect to $R_p$. Any potential detrimental measurement effects due to the physical properties of the electrodes themselves, in any conductivity measurement made, can be neglected, providing an accurate measurement of the actual conductivity of the electrolyte sample itself.

Referring to FIGS. 1 and 7, the conductivity measurement formed by the balanced conductivity measurement circuit 14 operates to compare a fixed known voltage parameter developed by the reference leg of the balanced circuit 14, with a measured voltage parameter, provided by the measurement leg of the balanced circuit 14. The resultant comparison yields an accurate measure of conductivity of the electrolyte sample within the measurement zone MZ of the probe 22. In the preferred embodiment, the circuits within the reference leg are operational mirror-images of the circuits within the measurement leg of the balanced circuit 14, with the exception of the detection polarity of the probe and reference detectors 25 and 19 respectively.

As is well known, the voltage gain factor of an operational amplifier such as the amplifiers 124 and 142, equals the impedance of the feedback loop divided by the input impedance to the inverting (−) input of the amplifier. The gain $A_r$ of the reference amplifier 16 is, therefore, the ratio of the impedances of the sum of the resistors 127 and 128, divided by the impedance of the resistor 123. The gain $A_r$, once set, will remain constant throughout all conductivity measurements.

Likewise, the gain $A_p$ of the probe amplifier 23 equals the impedance of its feedback network (comprising resistor 145 in series with the parallel combination of the resistor 146 and the impedance of the thermistor 58) all divided by the input impedance to amplifier 142, as represented by the impedance $R_p$ of the electrolyte sample. The gain $A_p$, therefore, will vary with both $R_p$ and with the varying resistance of the thermistor 58.

The thermistor 58 is inserted within the feedback loop of the amplifier 142 to compensate for changes in temperature of the electrolyte being measured. The thermistor 58 is required since electrolytes display a predictable temperature coefficient with conductance (i.e. in general the conductance of an electrolyte increases according to a positive temperature coefficient rate with temperature). To make the conductivity measurement of the electrolyte independent of its temperature, the thermistor 58 is selected and is connected in the feedback loop of the amplifier 142 so as to provide a temperature coefficient of conductance of the feedback network which is exactly the same as the temperature coefficient of conductance of the electrolyte. To aide in providing this function in the preferred embodiment, the thermistor 58 is a precision thermistor which insures repeatable performance over time. Further, as previously discussed, the thermistor is placed within the sample tube 41 so as to be negligibly effected by the temperature of the sample tube 41, enabling its output characteristic to truly reflect the temperature of the electrolyte sample within the measurement zone MZ. Since the impedance values of the thermistor 58 and of the electrolyte sample $R_p$ mathematically respectively appear in the numerator and in the denominator respectively of the gain equation which determines $A_p$, there effects exactly cancel one another, yielding a gain $A_p$ for the probe amplifier 23 which varies only with the actual electrolyte resistance $R_p$ and which is in this respect, independent of the electrolyte temperature.

The signal output of the probe amplifier 23 is filtered by the high pass filter 24 and is processed by the detector network 25 to provide a measurement output signal $V_p$ having positive polarity, to the summing junction 20. The signal output from the reference amplifier 16, is filtered by the high pass filter 18 and is processed by the detector network 19, to provide a reference output signal $V_r$ having negative polarity, to the summing junction 20. In the preferred embodiment, the filter networks 18 and 24 operate to suppress frequncies of less than 100 hz. The resistors 136 and 156 are matched to identically impede the $V_r$ and $V_p$ signals respectively, thus maintaining the balanced condition of the balanced measurement circuit 14. Since the detector networks 19 and 25 operate to provide output signals to the summing junction 20 which are opposite in polarity, in a truly balanced condition (i.e. wherein the gain factors $A_p$ and $A_r$ of the probe and reference amplifiers 23 and 16 respectively are equal) in the output signals $V_p$ and $V_r$ will identically cancel one another to provide a zero voltage signal input to the summing amplifier 28.

The conductivity meter is calibrated by drawing an electrolyte sample of known conductivity into the measurement zone MZ of the probe 22, by thereafter adjusting the gain $A_r$ of the reference amplifier 16 by means of the potentiometer 127 such that the gains $A_r$ and $A_p$ of the reference and probe amplifiers 16 and 23 respectively are identical, yielding a zero voltage input signal to the summing amplifier 28. Under these initial calibration conditions, the conductivity scale 30b of the conductivity measurement indicator 30 is positioned relative the indicator needle 30a so as to indicate that known conductivity, of the electrolyte sample under measurement. The conductivity of the sample thus measured will correspond to the lower range value on the conductivity scale 30b. The high range indication of the conductivity scale 30b is established by drawing an electrolyte sample of known conductivity, corresponding to the desired high range value for the conductivity meter, and by thereafter adjusting the potentiometer 29 until the indicator needle 30a of the indicator 30 aligns with the proper conductivity reading for that known electrolyte sample upon the conductivity scale 30b. The scale 30b can be thereafter linearly graduated between the thus established lower and upper range values in appropriate conductivity units. In the preferred embodiment, since the conductivity meter is employed to measure the conductance of a dialysate electrolyte for artificial kidney machines, the conductivity scale 30b is calibrated to indicate a condutivity range from 11 millimhos/cm to 15 millimhos/cm. It will be appreciated, however, that the particular conductivity range to be employed will vary depending upon the application to which the conductivity meter is put.

Once the conductivity measurement circuits have been calibrated as above described, direct conductivity measurements can thereafter be rapidly, accurately and automatically taken by simply dipping the probe 22 within the electrolyte and by reading the conductivity of the drawn electrolyte sample directly from the conductivity measurement indicator 30. No further adjustments or correlations are required; and each conductivity measurement will be independent of the temperature of the electrolyte being measured. The indicator 30 is energized directly by the summing amplifier 28 whose output signal is the amplifier algebraic sum of the output signals $V_p$ and $V_r$ respectively of the measurement and reference legs of the balanced measurement circuit 14.

The use of a balanced conductivity measurement circuit 14 offers significant advantages in providing accurate and repeatable measurements over time, without repeated recalibration of the system. Since a balanced measurement circuit is being employed, the measurement apparatus is independent of frequency or voltage variations of the AC output signal from the oscillator 10. Any frequency variations will identically be transmitted through the measurement and reference legs of the balanced circuit 14 and will cancel one another at the summing junction 20. Similarly, any voltage level fluctuations in the signal output from the oscillator 10 will be identically amplified by both the measurement and the reference legs of the balanced circuit 14, cancelling one another at the summing junction 20. The measurement circuit as disclosed is also relatively independent of the particular power supply voltage employed to energize the measurement circuits and requires no regulation of the supply voltage. Circuits of the preferred embodiment, accordingly, operate equally well from supply voltages ranging from 3 to 9 volts.

While we have disclosed a specific embodiment of our invention, it will be understood that this is for the purpose of illustration only, and that we are to be limited solely by the scope of the appended claims.

What is claimed is:

1. An improved portable dialystate conductivity meter for use with artificial kidney apparatus, comprising:
    a. an elongated probe of pen-like dimensions suitable for immersion within a dialysate bath, comprising:
        i. a sample tube having a wall enclosing an internal chamber for holding a sample of said dialysate, said internal chamber defining an elongate, generally cylindrical meausrement zone adjacent a first end of said pen-like probe, for isolating a fixed volume of said dialysate sample therein, said sample tube having an outer surface having an elongate flattened portion extending along said measurement zone;
        ii. a pair of spaced apart electrodes fixedly mounted to the flattened portion of said sample tube wall for projection within the meausrement zone of said internal chamber and having conductor terminals extending through said wall;
        iii. a thermistor fixedly mounted to the flattened portion of said sample tube wall for projection within the measurement zone of said internal chamber and having conductor terminals extending through said wall;
        iv. a flattened circuit pattern secured to said outer flattened portion of said sample tube wall and forming a plurality of conductors operatively connected to said conductor terminals of said thermistor and said pair of electrodes; and
        v. port means for said wall of said sample tube comprising an inlet port and an air release port respectively leading to opposite ends of said measurement zone, said inlet port providing a passageway for said dialysate to enter said measurement zone and said air release port providing a passageway for air to be displaced from said measurement zone, so as to operatively immerse said electrode pair and said thermistor whenever said probe is immersed a predetermined longitudinal depth within said dialysate; and
    b. AC excitation and measurement means operatively connected to said circuit pattern on said probe and to said pair of electrodes and said thermistor, for energizing said electrodes and said thermistor and for providing a conductivity output signal responsive to said energization which is accurately proportional to the electrical conductivity of that portion of said dialysate sample between said pair of electrodes.

2. A method of measuring the temperature compensated electrical conductivity of a dialysate for artificial kidney machines, comprising the steps of:
    a. causing a sample of the dialysate to be drawn into an internal measurement zone of a portable probe;

b. exposing said dialysate sample to a pair of spaced apart electrodes and to a thermistor within said measurement zone;

c. passing a fixed AC electrical signal between said spaced apart electrodes and through said dialysate sample within said measurement zone;

d. applying said signal thus passed through said dialysate sample to an active measurement branch of a balanced measurement circuit; e. varying the gain of said active measurement branch to compensate for the temperature of said dialysate by connecting said thermistor as a feedback element in said active measurement circuit;

f. applying said fixed AC electrical signal to an active reference branch of said balanced measurement circuit;

g. comparing the output signals of said active measurement and said active reference branches of said balanced measurement circuit; and h. providing an output signal indicative of the comparison of said output signals of said active balanced measurement circuit.

3. A portable dialysate conductivity meter for measuring the electrical conductivity of a dialysate bath for artificial kidney machines, comprising:

a. probe means for automatically drawing and isolating a sample of said dialysate within an internal measurement zone when immersed within said dialysate bath, said probe means including a pair of spaced-apart electrodes and a thermistor suspendedly mounted to project within said internal measurement zone, b. AC source means for providing an AC drive signal;

c. circuit means operatively connecting said pair of electrodes for energization by said AC drive signal, for establishing a resistive conductive path between said pair of electrodes through said dialysate sample within said internal measurement zone;

d. balanced measurement circuit means for providing a balanced output signal indicative of the conductivity of said dialysate sample within said internal measurement zone, comprising:

i. an active reference leg having reference amplifier means connected for energization by said AC drive signal and having a fixed reference gain factor, for producing a reference output signal in response thereto;

ii. an active measurement leg having probe amplifier means connected for energization from said pair of electrodes, operatively connected with said thermistor, and having a measurement gain factor cooperatively determined by said resistive conductive path through said dislysate sample and by the temperature dependent value of said thermistor, for producing a measurement output signal; and iii. summing means operatively connected to receive said reference output signal and said measurement output signal for providing said balanced output signal in response thereto which accurately varies with the conductivity of the dialysate sample.

4. A portable conductivity meter according to claim 3, wherein said probe amplifier means includes:

a. a probe amplifier having a signal input, a signal output and a feedback loop;

b. circuit means operatively connecting said signal input of said probe amplifier for energization from said pair of electrodes, presenting the resistive conductive path through said dialysate sample as the input resistance to said probe amplifier;

c. circuit means operatively connecting said thermistor within said feedback loop of said probe amplifier for temperature compensating the gain of said probe amplifier according to the temperature of said dialysate sample.

5. A portable conductivity meter according to claim 4, wherein said reference amplifier means within said reference leg of the balanced circuit includes an output detector network for causing said reference output signal to appear at a first polarity; and wherein said probe amplifier means includes an output detector network operatively connected to receive the signal output of said probe amplifier for causing said measurement output signal to appear at a second polarity, opposite to said first polarity.

6. A portable conductivity meter according to claim 5, wherein said summing means comprises a summing amplifier operatively connected to receive said detected reference and measurement output signals for providing said balanced output signal which equals the algebraic sum of said detected reference and measurement output signals.

7. A portable conductivity meter for measuring the electrical conductivity of a dialysate bath in artificial kidney machines, comprising:

a. probe means immersible within said dialysate bath for drawing a sample thereof, comprising:

i. a sample tube defining an enclosed internal chamber for holding said dialysate sample and having a measurement zone therein;

ii. port means cooperatively connected with the internal chamber of said sample tube for causing said measurement zone to automatically fill with said dialysate when said probe means is immersed therein; and iii. a pair of spaced-apart electrodes mounted for projection within said measurement zone; and b. measurement circuit means for providing an accurate measurement of the electrical conductivity of said dialysate smaple within said measurement zone, comprising:

i. AC source means for providing an AC drive signal;

ii. circuit means connecting said pair of electrodes for energization by said AC drive signal, establishing a conductive path therebetween through said dialysate sample contained within said measurement zone;

iii. balanced circuit means including balanced active reference and measurement circuit branches respectively having reference and measurement gain factors for providing reference and measurement output signals when energized by an AC signal;

iv. means for energizing said balanced circuit means by said AC drive signal;

v. means connecting said pair of electrodes with said measurement branch of said balanced circuit means for varying said measurement gain factor in response to current flow through said dialysate sample contained within said measurement zone; and vi. output circuit means operatively connected to receive said reference and said measurement output signals for providing an indicator output signal in response thereto, said indicator output signal accurately varying according to the conductivity of the dialysate sample located between the pair of electrodes within the measurement zone.

8. A portable conductivity meter according to claim 7, wherein said probe means is further characterized by:
   a. said sample tube comprising an elongate tube, wherein said measurement zone comprises a longitudinal length of said internal chamber of said sample tube; and
   b. said port means comprising first and second spaced-apart port openings into said internal chamber at opposite ends of said measurement zone, providing a continuous path for flow of said dialysate sample through said internal chamber therebetween, wherein said first port causes said dialysate sample to enter said measurement zone when said probe means is immersed within said dialysate bath and said second port causes air within said internal chamber to escape as said dialysate sample fills said measurement zone.

9. A portable conductivity meter according to claim 8, wherein said circuit means connected for energizing said pair of electrodes by said AC drive signal comprises an elongate length of flexible electrical cable secured to said probe means near its said second port in a manner causing said probe means to become suspendable from said cable such that said first and second ports are generally vertically oriented with said first port positioned below said second port.

10. A portable conductivity meter according to claim 8, wherein said sample tube includes an outer flattened surface longitudinally extending along said measurement zone, wherein said pair of spaced-apart electrodes are mounted to project through the wall of said sample tube from said flattened surface thereof, and wherein said circuit means connecting said pair of electrodes for energization by said AC drive signal includes an electrical conductor pattern secured to said outer flattened surface of said sample tube and operatively electrically connected with said pair of electrodes.

11. A portable conductivity meter according to claim 10, wherein said electrical conductor pattern comprises a printed circuit pattern bonded to said outer flattened surface of said sample tube.

12. A portable conductivity meter according to claim 10, wherein said probe means includes protective means for covering said sample tube and for electrically insulating said conductor pattern and electrical connections thereto from the external environment in a manner such that said first and second port openings provide a continuous path from the external environment into said internal chamber of the sample tube.

13. A portable conductivity meter according to claim 7, wherein said measurement circuit means includes compensation circuit means operatively connected with said balanced circuit means for rendering the electrical conductivity measurement of said dialysate sample independent of the temperature of said dialysate sample.

14. A portable conductivity meter according to claim 13, wherein said measurement circuit branch of said balanced circuit means includes an active amplifier having said measurement gain factor; wherein said means connecting said pair of electrodes with said measurement branch operatively connects said electrode pair to provide an equivalent input resistance to said amplifier, said equivalent resistance being indicative of the electrical conductance of said dialysate sample within said measurement zone; wherein said temperature compensation means includes a thermistor mounted for projection within said sample tube measurement zone and means for connecting said thermistor within a feedback loop of said active amplifier within said measurement branch for varying in combination with said input impedance thereto said measurement gain factor of said amplifier.

* * * * *